US008370172B2

(12) United States Patent
Shell et al.

(10) Patent No.: US 8,370,172 B2
(45) Date of Patent: Feb. 5, 2013

(54) SYSTEM AND METHOD FOR SUBMITTING MEDICATION CLAIMS BY POINT-OF-CARE PHYSICIANS

(75) Inventors: William E. Shell, Los Angeles, CA (US); Elizabeth Charuvastra, Los Angeles, CA (US)

(73) Assignee: Targeted Medical Pharma, Los Angeles, CA (US)

( * ) Notice: Subject to any disclaimer, the term of this patent is extended or adjusted under 35 U.S.C. 154(b) by 1010 days.

(21) Appl. No.: 11/804,085

(22) Filed: May 17, 2007

(65) Prior Publication Data

US 2008/0288281 A1  Nov. 20, 2008

(51) Int. Cl.
*G06Q 50/00* (2012.01)
(52) U.S. Cl. .................................. 705/2; 705/3; 705/4
(58) Field of Classification Search .................. 705/2–4
See application file for complete search history.

(56) References Cited

U.S. PATENT DOCUMENTS

| | | | | |
|---|---|---|---|---|
| 5,235,702 | A | * | 8/1993 | Miller ............................ 707/102 |
| 5,704,044 | A | | 12/1997 | Tarter et al. |
| 5,960,411 | A | | 9/1999 | Hartman et al. |
| 6,070,148 | A | | 5/2000 | Mori et al. |
| 6,070,149 | A | | 5/2000 | Tavor et al. |
| 7,346,523 | B1 | * | 3/2008 | Provost et al. .................... 705/4 |
| 2007/0033070 | A1 | * | 2/2007 | Beck et al. ......................... 705/2 |

OTHER PUBLICATIONS

Health Insurance Claim Form 1500 (National Uniform Claim Committee, Aug. 2005 revision).*

* cited by examiner

*Primary Examiner* — Gerald J. O'Connor
*Assistant Examiner* — Mark Holcomb
(74) *Attorney, Agent, or Firm* — Belair & Perrone LLP (57) ABSTRACT

A system for submitting a claim for a dispensed medication to a patient by a point-of-care physician including means acquiring at least one of the group consisting of a national practitioner number and a non pharmacy dispensing number for the point-of-care physician; means for displaying to a user a selection of data fields relating to the claim; means for inputting into the data fields data relating to the claim including the at least one of the group consisting of the national practitioner identifier number and the non pharmacy dispensing number; means for transmitting to a logic switch the claim containing the at least one of the group consisting of a national practitioner identifier number and a non pharmacy dispensing number identifying the point-of-care physician for determining the processor for the claim; means for determining the pathway for the claim based on a type of payor associated with the patient; means for processing the claim containing the at least one of the group consisting of a national practitioner identifier number and a non pharmacy dispensing number to identify the point-of-care physician; and responsive to the means for processing, means for transmitting to the point-of-care physician an adjudication regarding the claim.

14 Claims, 9 Drawing Sheets

| BillDefID | BillID | MEDICATION PRESCRIBED | UNITS |
|---|---|---|---|
| 1 | 6 | HYPERTENSA | 2 |
| 2 | 19 | HYPERTENSA | 1 |
| 3 | 18 | SENTRAAM | 1 |
| 4 | 18 | APPTRIM | 1 |
| 5 | 7 | LYTENSOPRIL | 1 |
| 6 | 8 | PRAZOLAMINE | 1 |
| 7 | 26 | SENTRA AM | 1 |
| 8 | 25 | SENTRA AM | 1 |
| 9 | 24 | SENTRAPM | 2 |
| 10 | 28 | SENTRA AM | 1 |
| 11 | 28 | SENTRA PM | 1 |
| 12 | 6 | APPTRIM | 1 |
| 13 | 28 | THERAMINE | 1 |
| 14 | 30 | SENTRA AM | 1 |
| 15 | 30 | THERAMINE | 4 |
| 16 | 29 | THERAMINE | 1 |
| 17 | 32 | SENTRA AM | 4 |
| 18 | 1 | APPTRIM | 3 |
| 19 | 2 | SENTRAPM | 2 |
| 20 | 2 | HYPERTENSA | 4 |
| 21 | 2 | APPTRIM | 1 |
| 22 | 5 | APPTRIM | 1 |
| 23 | 6 | APPTRIM | 2 |
| 24 | 32 | SENTRA AM | 4 |
| 25 | 27 | SENTRAAM | 1 |
| 26 | 38 | SENTRA PM | 1 |
| 27 | 42 | SENTRAAM | 1 |
| 28 | 42 | SENTRA PM | 1 |
| 29 | 42 | THERAMINE | 1 |
| 30 | 39 | SENTRA AM | 1 |
| 31 | 39 | SENTRA PM | 1 |
| 32 | 39 | THERAMINE | 2 |
| 33 | 35 | SENTRAAM | 1 |
| 34 | 6 | HYPERTENSA | 4 |
| 35 | 34 | SENTRAAM | 2 |
| 36 | 34 | SENTRA PM | 2 |
| 37 | 36 | SENTRA AM | 1 |
| 38 | 37 | SENTRA PM | 1 |
| 39 | 33 | THERAMINE | 2 |
| 40 | 41 | SENTRA AM | 2 |
| 41 | 40 | THERAMINE | 1 |

*FIG. 3*

*FIG. 4*   CONFIDENTIAL PATIENT INFORMATION - DO NOT DISCLOSE

TRANSACTION RESPONSE SUMMARY:
- 404 — Transmitted to ------- PART D HUMANA — 402 (HUMANAD
- Switch used ------- ENV
- Patient ID ------- ######### — 406
- 408 — Rx reference number ------- #########
- Date of service ------- 12/18/2006 — 410
- 412 — Transaction type ------- BY BILLING
- Transaction status ------- REJECTED — 414

ROUTING INFORMATION USED:
- BIN Number ------- ######### — 416
- 418 — Processor Control Number ------- #########
- Service Provider ID ------- ######### — 420
- 422 — Software vendor ID ------- #########
- Date of transmission ------- 12-21-2006
- Time of transmission ------- 14:03:09

MESSAGE INFORMATION RECEIVED:
- F4 Message -------

STATUS INFORMATION RECEIVED:
- AN Transaction Response Status ------- R — 424
- 426 — FB Reject Code ------- A5 (Not covered under part D law)
- FB Reject Code ------- 70 (Product/Service Not Covered)
- 430 — FQ Additional Message Information ------- CMS EXCLUDED DRUG — 428

CLAIM INFORMATION RECEIVED:
- EM &/Service Reference Qualifier ------- #########
- 434 — D2 Prescription/Service Number ------- ######### — 432

INSURANCE INFORMATION SUBMITTED:
- C2 Cardholder ID ------- ######### — 436
- 438 — C1 Group ID ------- #########
- C6 Patient Relationship Code ------- ######### — 440
- 442 — CC Cardholder First Name ------- #########
- CD Cardholder Last Name ------- #########
- 446 — CE Home Plan ------- ######### — 444

PATIENT INFORMATION SUBMITTED:
- C4 Date Of Birth -------

GENERAL CLAIM INFORMATION SUBMITTED:
- EM Rx/Service Reference Qualifier ------- ######### — 448
- 450 — D2 Prescription/Service Number ------- #########
- E1 Product/Service ID Qualifier ------- ######### — 452
- 454 — D7 Product/Service ID ------- ######### — 456
- CW Alternate ID ------- #########
- 458 — D3 Fill Number ------- ######### — 460
- D5 Days Supply ------- #########
- 462 — D8 DAW/Product Selection Code ------- ######### — 464
- DE Date Prescription Written ------- #########
- 466 — DF Number of Refills Authorized ------- #########
- DI Level Of Service ------- ######### — 468
- 470 — DJ Prescription Origin Code ------- #########
- DK Submission Clarification Code ------- ######### — 472
- 474 — DT Unit Dose Indicator ------- #########
- E7 Quantity Dispensed ------- ######### — 476
- 478 — EU Prior Auth Type Code ------- #########
- 28 Unit of Measure ------- ######### — 480

PRICING INFORMATION SUBMITTED:
- 482 — D9 Ingredient Cost Submitted ------- #########
- DN Basis Of Cost Determination ------- ######### — 484
- 486 — DQ Usual and Customary Charge ------- #########

PRESCRIBER INFORMATION SUBMITTED:
- EZ Prescriber ID Qualifier ------- ######### — 488

*FIG. 6*

| PLEASE DO NOT STAPLE IN THIS AREA | | HEALTH INSURANCE CLAIM FORM 600 | pICA |
|---|---|---|---|
| 1. MEDICARE  MEDICAID  CHAMPUS  CHAMPVA  GROUP HEALTH PLAN  FECA BLK LUNG  OTHER | | 1a. INSURED'S I.D. NUMBER  602  604 | (FOR PROGRAM IN ITEM 1) |
| ☐(Medicare#) ☐(Medicaid #) ☐(Sponsor's SSN) ☐(VA File #) ☐(SSN or ID) ☐(SSN) ☐(ID) | | | |
| 2. PATIENT'S NAME (Last Name, First Name, Middle Initial) | 3. PATIENT'S BIRTHDATE  SEX  MM  DD  YY  M☐ F☐ | 4. INSURED'S NAME(Last Name, First Name, Middle Initial) | |
| 5. PATIENT'S ADDRESS (No. Street) | 6. PATIENT RELATIONSHIP TO INSURED  Self☐ Spouse☐ Child☐ Other☐ | 7. INSURED'S ADDRESS(No. Street) | |
| CITY  STATE | 8. PATIENT STATUS  (ID)  Single☐ Married☐ Other☐  Employed☐ Full-Time Student☐ Part-Time Student☐ | CITY  STATE | |
| ZIP CODE  606  TELEPHONE(INCLUDE AREA CODE) ( ) | | ZIP CODE 610  TELEPHONE(INCLUDE AREA CODE) ( ) | |
| 9. OTHER INSURED'S NAME (Last Name, First Name, Middle Initial) 608 | 10. PATIENT'S CONDITION RELATED TO: a. employment (current or previous) ☐YES ☒NO | 11. INSURED'S POLICY GROUP OR FECA NUMBER | |
| a. OTHER INSURED'S POLICY OR GROUP NUMBER | | a. INSURED'S DATE OF BIRTH  MM  DD  YY  SEX  M☐ F☐ | |
| b. OTHER INSURED'S DATE OF BIRTH  SEX  MM  DD  YY  M☐ F☐ | b. AUTO ACCIDENT?  PLACE (State) ☐YES ☒NO | | |
| | c. OTHER ACCIDENT? | b. EMPLOYER'S NAME OR SCHOOL NAME | |
| c. EMPLOYER'S NAME OR SCHOOL NAME | ☐YES ☒NO | c. INSURANCE PLAN NAME OR PROGRAM NAME | |
| d. INSURANCE PLAN NAME OR PROGRAM NAME | 10d. RESERVED FOR LOCAL USE | d. IS THERE ANOTHER HEALTH BENEFIT PLAN?  ☐YES ☐NO If yes, return to and complete item 9a-d | |
| READ BACK OF FORM BEFORE COMPLETING & SIGNING THIS FORM.  12. PATIENT'S OR AUTHORIZED PERSON'S SIGNATURE authorize the release of any medical or other information necessary to process this claim. I also request payment of government benefits either to myself or to the party who accepts assignment  SIGNED ________ DATE ________ | | 13. INSURED'S OR AUTHORIZED PERSON'S SIGNATURE: authorize payment or medical benefits to the undersigned physician or supplier for services described below.  SIGNED ________ | |
| 14 DATE OF CURRENT  MM  DD  YY  ILLNESS (First symptom) OR INJURY (Accident) OR PREGNANCY(UMP) | 15. IF PATIENT HAS HAD SAME OR SIMILAR ILLNESS GIVE FIRST DATE  MM  DD  YY | 16. DATES PATIENT UNABLE TO WORK IN CURRENT OCCUPATION  FROM  MM  DD  YY  TO  MM  DD  YY | |
| 17. NAME OF REFERRING PHYSICIAN OR OTHER SOURCE | 17a. I.D. NUMBER OR REFERRING PHYSICIAN 612 | 18. HOSPITALIZATION DATES RELATED TO CURRENT SERVICES  FROM  MM  DD  YY  TO  MM  DD  YY | |
| 19. RESERVED FOR LOCAL USE | | 20. OUTSIDE LAB?  ☐YES ☐NO | $ CHARGES |
| 21. DIAGNOSIS OR NATURE OF ILLNESS OR INJURY. (RELATE ITEMS 1,2,3 OR 4 TO ITEM 24E BY LINE)  1. ⌐3004  3. ⌐____  2. ⌐____  4. ⌐____ | | 22. MEDICAID RESUBMISSION CODE  ORIGINAL REF. NO. | |
| | | 23. PRIOR AUTHORIZATION NUMBER | |

| 24. | A | B | C | D | E | F | G | H | I | J | K |
|---|---|---|---|---|---|---|---|---|---|---|---|
| 618 | DATE(S) OF SERVICE 614  FROM   TO  MM DD YY  MM DD YY | PLACE OF SERVICE | TYPE OF SERVICE 616 | PROCEDURE SERVICES OR SUPPLIES (Explain Unusual Circumstances)  OPTIM...  MODIFIER | DIAGNOSIS CODE 620 | $CHARGES | DAYS OR UNITS | EPSOT FAMILY PLAN | EMG | CDS | RESERVED FOR LOCAL USE |
| | Default Values! | | | | | 0 00 1 | | | | | |
| | This page shows the patient record. If you want to print a claim, click on the Charges tab then click the Print 150 button. | | | 630 | | 622 624 | | | | | |
| | | | | | | 626 | | 628 | | | |

| 25. FEDERAL TAX ID NUMBER  SSN  EN  ☐  ☐ | 26. PATIENTS ACCOUNT NO. | 27. ACCEPT ASSIGNMENT (For good, check see back)  ☐YES ☐NO | 28. TOTAL CHARGE $ | 29. AMOUNT PAID $  0 00 | 30. BALANCE DUE $ |
|---|---|---|---|---|---|
| SIGNATURE OF PHYSICIAN OR SUPPLIER INCLUDING DEGREES OR CREDENTIALS (I certify that the statements on the reverse apply to this bill and are made a part....)  Signed ________ Date ___  632 | 32. NAME AND ADDRESS OF FACILITY WHERE SERVICES WERE RENDERED (if other than home or office) | | 33. PHYSICIAN'S SUPPLIER'S BILLING NAME, ADDRESS, ZIP CODE & PHONE #  SIGNED ________ DATE ___ | | |

| | 902 | | Contact by Organization | Name | |
|---|---|---|---|---|---|
| Name | Specialty | Group | Office Mgr | Physician Notes | |
| | | | | | |
| Address | Address | City | State | Zip Code | |
| | | | | | |
| Bus Phone | Cell Phone | Fax No. | Email | Zip | |
| | | | | | |
| Name | Specialty | Group | Office Mgr | Physician Notes | |
| | | | | | |
| Address | Address | City | State | Zip Code | |
| | | | | | |
| Bus Phone | Cell Phone | Fax No. | Email | Zip | Ctry |
| | | | | | |

| Billing | Actions | | | | | | | |
|---|---|---|---|---|---|---|---|---|
| Patient Name | Specialty | | Date | Input Date | | Bill | | |
| | | | | | | | | |
| Claim Notes | | | | | | | | |
| | | | | | | | | |
| Chg Status | | Chgawp | Chgsrp | | Chagmac | Claim Total | | |
| | | | | | | | | |
| Actions | Medications Prescribed | # of Units | Unit Price | Unit Pack | Unit Total | Billing Services | Chg Status | Chg Date |
| A | | | 147.5 | 2 | 295 | | | |
| A | | | | | | | | |
| | | | 295 | | | | | |
| Record 1 of 1 | | | | | | | | |

FIG. 11

| Actions/Address | Contact | Contract | Position |
|---|---|---|---|

| | View/Edit Action Type | | View/Edit Address Type |
|---|---|---|---|
| | Action Type | | Address Type |
| | Document Sent | | Alt Office |
| | Email Rcvd | | Bill To |
| | Email Sent | | Home |
| | FaxRcvd | | Pay To |
| | Fax Sent | | Primary Office |
| | Letter Rcvd | | Sales Office |
| | Letter Sent | | Sales Office |
| | Meetings Arranged | | Second Office |
| | Meeting Held | | Service Office |
| | Phone Call Made | | Service Office |
| | ⋮ ⋮ | | ⋮ ⋮ |

SYSTEM AND METHOD FOR SUBMITTING MEDICATION CLAIMS BY POINT-OF-CARE PHYSICIANS

FIELD OF THE INVENTION

The present invention relates to a method and system for billing third party insurance companies for pharmaceuticals, medical foods, and co-packed or combination products with pharmaceuticals co-packed or combined with medical foods ("dispensed medications"), and more particularly for point-of-care practitioners who directly dispense these products to directly submit claims to third party insurance companies for dispensed medications to patients by physicians.

PROBLEM

Until recently, point of care practitioners, such as physicians, dispensing medications in their offices was not a common practice due to cultural barriers, inventory barriers and liability concerns. User-friendly and affordable software has now made it more practical for physicians to manage inventory, track prescribing habits, maintain patient and invoice records, and check for drag interactions. With the introduction of sophisticated software to support dispensing physicians and changing economics of medical practice, the percentage of physicians dispensing medication has risen to an estimated 7 percent to 10 percent. Nevertheless, dispensing of pharmaceuticals to patients by point-of-care physicians has been limited to direct cash payments by the patients, because systems to bill third party insurance companies ("payors") have not existed for physicians.

The growth of physicians dispensing pharmaceuticals to patients is related to several reasons: (i) the need to increase physician income within the managed care and falling reimbursement environment, (ii) the need to reduce the $5-$7 per pharmacy call-back costs of the average practice, (iii) the substantial savings to insurers afforded by point-of-care dynamics, (iv) the reduced error rates associated with physician dispensing, (v) the increased patient compliance associated with physician dispensing, and (vi) the preference or tendency of dispensing physicians to choose generics rather than more expensive brand product for their patients.

The largest impediment to growth of physician dispensing is the complexity of obtaining third party re-imbursement for dispensed medications. Physicians cannot submit insurance claims for medications despite their ability to dispense them. The pharmaceutical industry in the United States and other developed countries is primarily a third party payment system Insurance systems act as payors rather than the patients. The inability of physicians to submit a claim and adjudicate the response presents several problems for physician service providers, including the following: (i) delays in receipt of payment, (ii) difficulty in reconciling accounts and payments, (iii) unilateral adjustments by processors of approved adjudications, (iv) increasing credit risks among payors and obligors, (v) incertainty of approvals, and (vi) assorted charges per claims transaction.

A further problem is the inability of physicians to identify themselves as dispensing physicians and to be entitled to payment from payors. Until October 2006, there was not a unique physician's identifier in the U.S. Various numbers have been used to identify physicians including a State License Number, a Drug Enforcement Agency number, a Medicare pin number, and tax numbers. In October 2006, a national practitioner identification number ("NPI number") was implemented to fully take effect in April 2007. Currently, each of the payors plans has a different system for identifying physician as either providers or prescribers. Similarly, there were no identification numbers to uniquely identify pharmacy providers. Recently, the National Council for Prescription Drug Programs numbers ("NCPDP numbers") have evolved that uniquely identify pharmacies, but not physicians.

SOLUTION

The above-described problems are solved and a technical advance achieved by the system and method for point-of-care physicians to submit claims to third party payors for dispensed medications ("physician dispensed medication claim submittal system"). One aspect of the present physician dispensed medication claim submittal system enables access to third party payors by physicians.

The present physician dispensed medication claim submittal system described herein includes an interface to existing pharmacy systems that enable a point-of-care physician to utilize the existing NCPDP 5.1 interface system. The present physician dispensed medication claim submittal system includes gathering information with forms, transmitting information to a claims processing center via a secure interface, accessing a logical switch where the pathway to a reimbursable bill is determined, entering of the data into an interface that either uses a national practitioner identifier number ("NPI number") and/or a non-pharmacy dispensing site number ("NPDS number") to identify the physicians eligibility to enter a NCPDP 5.1 compliant switch. In addition, the present physician dispensed medication claim submittal system receives an adjudication response that is retransmitted to the physician, which heretofore was not available to physicians.

The present physician dispensed medication claim submittal system provides physician providers, such as point-of-care physicians, with the capability of dispensing dispensed medications to a patient, selecting the appropriate pathway for filing for insurance reimbursement, and obtaining adjudication information. The present physician dispensed medication claim submittal system enables a point-of-care physician to submit a claim for dispensed medications, process the claim, and facilitate the delivery of the reimbursement payment to the physician.

SUMMARY

A system for submitting a claim for dispensed medications to a patient by a point-of-care physician including a means of acquiring at least one of the group consisting of a NPI number and/or a NPDS number for the point-of-care physician; a means for displaying to a user a selection of data fields relating to the claim; a means for inputting into the data fields data relating to the claim including the at least one of the group consisting of the NPI number and/or the NPDS number, a means for transmitting to a logic switch the claim containing the at least one of the group consisting of a NPI number and a NPDS number identifying the point-of-care physician for determining the processor for the claim; a means for determining the pathway for the claim based on a type of payor associated with the patient; a means for processing the claim containing the at least one of the group consisting of a NPI number and a NPDS number to identify the point-of-care physician; and responsive to the means for processing, a means for transmitting to the point-of-care physician an adjudication regarding the claim.

BRIEF DESCRIPTION OF THE DRAWINGS

FIG. 4 illustrates an exemplary screen shot of a GUI of a Form UDF for submitting dispensed medication claims by point-of-care physicians according to an embodiment of the present mention;

FIG. 6 illustrates an exemplary screen shot of a GUI of a Form 1500 for submitting dispensed medication claims by point-of-care physicians according to an embodiment of the present invention;

DETAILED DESCRIPTION OF THE DRAWINGS

Service providers or point-of-care physicians mean physicians who sell dispensed medications to their patients. In another sense, it may mean the employees, such as claims processors located at the service providers office. Plan sponsor means an entity that sponsors a group and/or groups of consumers receiving health care benefits. A plan sponsor may be an insurance company that collects premiums directly from consumers in return for insurance benefits. Some examples of plan sponsors include commercial insurance companies, health maintenance organizations ("HMOs"), preferred provider organizations ("PPO"), Blue Cross/Blue Shield entities, affinity groups, unions, government entitlement programs (for example, Medicaid), self-insured private and government employers (i.e., employers that take on the direct responsibility and liability for the health care claims for their employees rather than purchase third-party coverage for such claims from commercial insurers), and private and governmental employers that are not self-insured. It is estimated that more than 4,000 insurance plans exists today. There are multiple Medicare sponsors for Part B Medicare and at least 98 Medicare Part D plan sponsors. The present physician dispensed medication claim submittal system enables physicians to submit claims for dispensed medications that are sold through their offices to members of plan sponsors.

An obligor means an entity that is generally considered ultimately responsible for making payments for healthcare services provided for on its behalf and for the insurance risk associated with a particular plan. The current online pharmaceutical network recognizes an estimated 4,500 entities as obligors. An obligor may also function as an administrator, as is the case with certain insurance carriers, or as a payor or processor. Most of the obligors recognized by the online pharmaceutical network utilize separate entities that perform these functions to facilitate their prescription programs.

An administrator, often called a third-party administrator ("TPA"), means an entity that designs, structures, and services prescription plans on behalf of another. A plan means a set of parameters that indicates the eligibility and types of insurance coverage of a particular group of insured consumers. TPAs also maintain service provider networks and enroll and contract with pharmacies on behalf of obligors. Some TPAs also provide payment services for obligors. They may bill the obligor for approved claims on a regular basis and remit payments to the service provider on behalf of the plan sponsor. TPAs may also subcontract certain functions to payors and processors.

A payor means an entity, usually a TPA or obligor that issues payments to service providers on behalf of obligors. A payor also provides obligors with management reports and sends service providers, along with payment, a remittance advice ("RA") (i.e., a report outlining those transactions that have been handled and positively adjudicated in the indicated processing cycle, along with any adjustments and processing charges) together with the payment. The total amount indicated on the RA should equal the amount of the payment, which it accompanies.

A processor means an entity that provides online and paper-based manual adjudication services. An adjudication means a decision as to acceptance, rejection, suspension, and payment of a particular pharmaceutical claim. A processor's responsibility is to adjudicate pharmaceutical claims by applying the plan parameters established by the TPA (i.e., determining the acceptability of a claim based, for example, on a claimant's eligibility, medication, and price) and to report the results to the service provider. Typically, each payor selects a standard reimbursement payment cycle, typically 14 or 30 days, during which the processor further adjudicates claims submitted over the online network by service providers and pay the claim. The present physician dispensed medication claim submittal system enables physicians to submit claims to the processor for dispensed medications to a patient or customer.

A switch provides a means for relaying electronic claims data from service providers to processors. Based upon a Bank Identification Number ("BIN"), a unique number issued by the American National Standards Institute, which identifies the appropriate processor, the switch forwards messages from the service provider to the processor and returns the responses. In general, a switch does not impact the content of any of the messages it processes, but is merely a communications conduit.

Switches accept industry standard formatted messages from pharmacies. The three largest switches—National Data Corporation, of Atlanta, Ga. ("NDC"), Envoy Corporation, of Memphis, Tenn., and General Computer Corporation, of Twinsburg, Ohio—process approximately 80% of all online transaction volume, with NDC being responsible for 70% of this volume and being the only switch with access to every major processor.

Existing software used by pharmacies today varies dramatically, however, the functions they perform and the formats used to transmit third party pharmacy claims are essentially identical, because all electronic messages must conform to the standard electronic message format set by the National Council for Prescription Drug Programs ("NCPDP") of Phoenix, Ariz. NCPDP provides standard formats for many electronically transmitted message formats, including, for example, the following formats which specify field number, field name, field type, field format, and field length positions: (i) transaction format for prescription, which includes fields such as BIN, version number, transaction code, processor code, pharmacy number, group number, cardholder identification number, date of fill, and prescription number, (ii) response format for eligibility verification or prescription claim, which includes fields such as BIN, transaction code, response status, and response data; and (iii) claim reversal format, which includes fields, such as BIN, transaction code, processor code, pharmacy identification number, date of fill, and prescription number. Other NCPDP standard message formats include a worker's compensation claim format, a Medicaid claim format, a claim payable response format, and a claim captured response format. The present physician dispensed medication claim submittal system utilizes these NCPDP standard formats in implementing new functionality into the current system to enable claim input from physicians dispensing and selling pharmaceuticals.

Figures 1, 5:
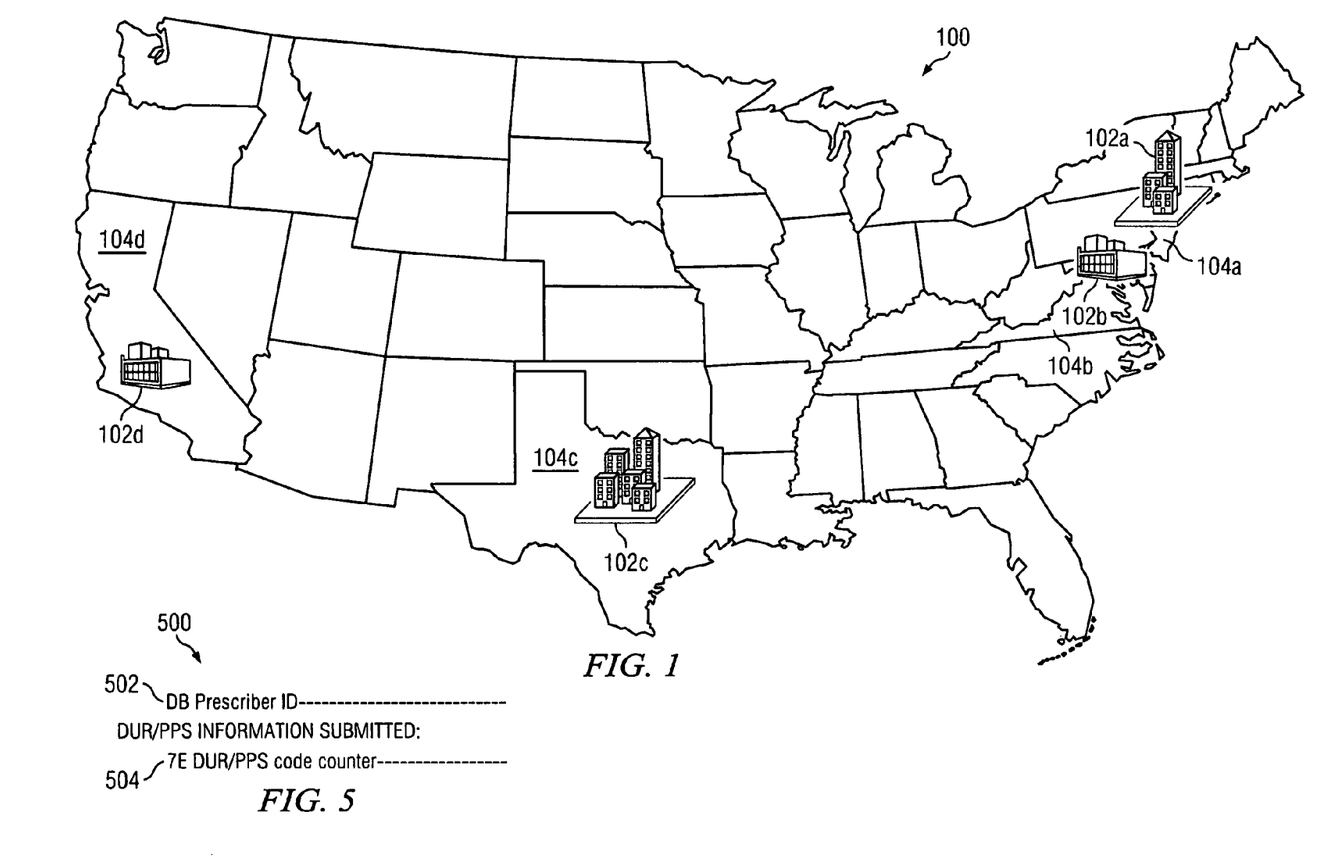
FIG. 1 illustrates a map of an exemplary number of physician's offices and a third party payor office according to an embodiment of the present invention.
FIG. 5 illustrates the exemplary screen shot of a GUI of the Form UDF of FIG. 4 for submitting dispensed medication claims by point-of-care physicians according to an embodiment of the present invention.

Like reference numerals are used to indicate like parts throughout the drawings. FIG. 1 is a map 100 that includes an exemplary assortment of point-of-care physician's offices 102b-102d, each in a different state 104b-104d. A processor's office 102a may be located in Washington, D.C., as shown. The processor's office 102a typically includes employees, data-entry employees, clerical employees, data-management employees, collectors, engineers, accountants, technicians, and the like that operate the processor's office 102a. The processor's office 102a may further include a CEO, management committee, human resources administration, marketing administration, and other administration functions.

Figure 2:
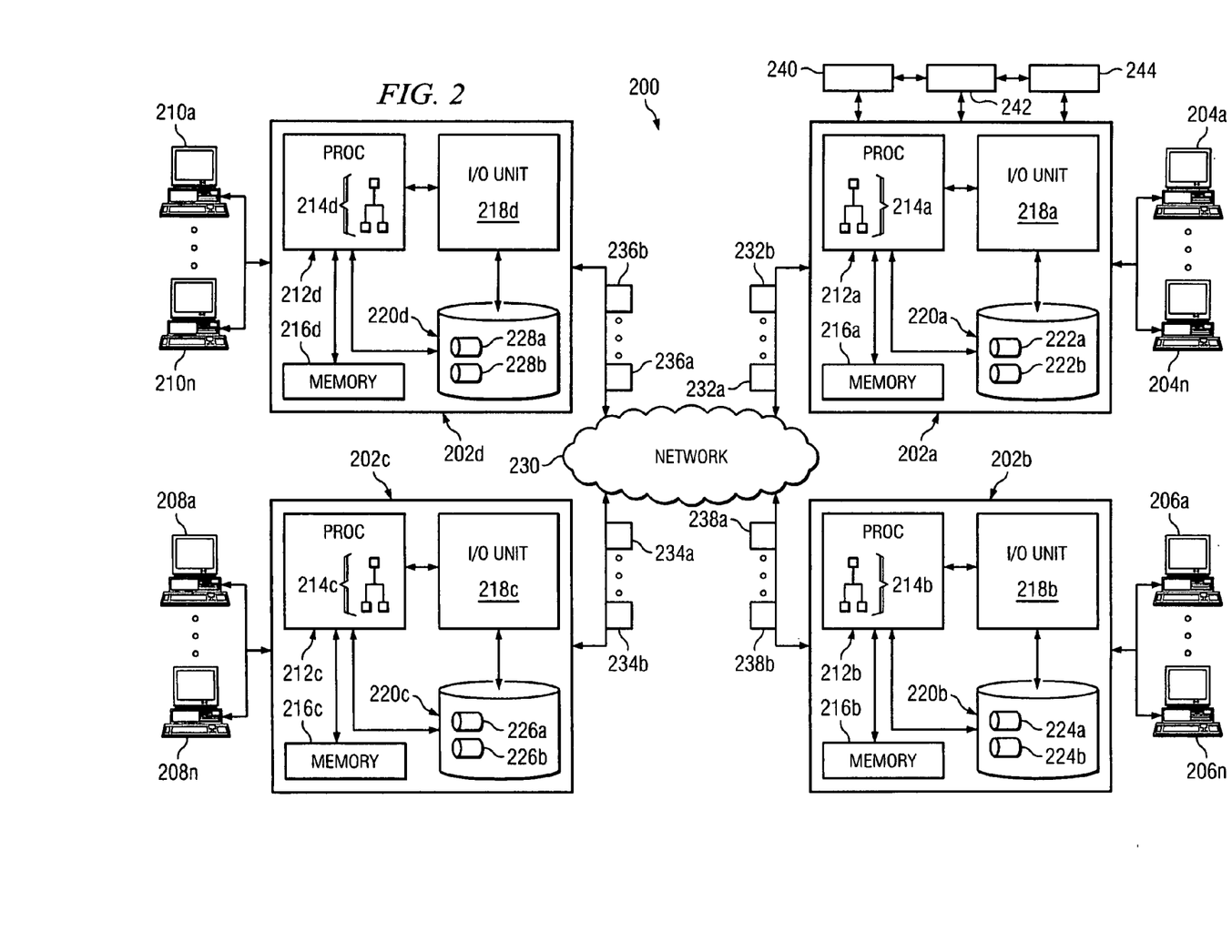
FIG. 2 illustrates a block diagram of an exemplary network of computers in a system for providing physicians access to the third party payor for submitting claims directly to the third party payor for dispensed medications by the physician to their patients according to an embodiment of the present invention.

FIG. 2 is a block diagram of an exemplary network of computers 200 utilized by the present physician dispensed medication claim submittal system, such as that shown in FIG. 1. Processor office 102a may utilize server 202a and the point-of-care physician's offices 102b-102d may utilize server 202b, 202c, and 202d, respectively, (202a-202d collectively 202). The servers 202 may host personal computers 204a-204n, 206a-206n, 208a-208n, and 210a-210n, respectively, utilized by the employees or users of the processor's office 102a and the point-of-care physician offices 102b-102d.

The server 202a may include a processor 212a that executes software 214a. The processor 212a may be in communication with memory 216a, an input/output (I/O) unit 218a, and a storage unit 220a. The storage unit 220a may store databases or data repositories 222a-222b thereon. The software 214a may include instructions for execution by the processor 212a for providing network connectivity and computer status information in accordance with the principles of the present physician dispensed medication claim submittal system. In one embodiment, the software 214a is composed of a pharmaceutical claim submittal, patient information submittal, patient insurance submittal and reimbursement software program further described herein. The server 202a may be physically located or utilized by the processor office 102a.

A point-of-care physician office may utilize the server 202b. The server 202b may include a processor 212b that executes software 214b. The processor 212b may be in communication with memory 216b, I/O unit 218b, and storage unit 220b. The storage unit may store databases 224a-224b for storing information associated with the computers and networks in the point-of-care physician office. Each of the other point-of-care physician offices may utilize the servers 202c and 202d, which may include the same or similar internal components as those of servers 202a and 202b, which are shown, accordingly. Each of the servers 202 may communicate via a network 230. The network 230 may be the Internet, intranet, WANs, LANs, or other communication systems capable of communicating information between computing devices. The server 202a may communicate data packets 232a-232b containing information related to any of the computer and networks of the company to another server 202b through data packets 238a-238b, as understood in the art. Similarly, the servers 202c and 202d may communicate information to the server 202a via data packets 234a-234b and 236a-236b, respectively, via the network 230. In addition, network 230 may be a communications network a computer network an internet network or a combination of them, and the like. In one embodiment, the entry forms are operated through a SharePoint server over the Internet.

In operation, the server 202a may execute the software 214a to enable the point-of-care physician offices to utilize their personal computers 206a-210n, for example, either directly with the server 202a or indirectly via the network 230. The personal computers 206a-210n enable the employees of the point-of-care physician offices to interface with the software 214a to display pharmaceutical claim submittal and reimbursement information. Personal computers 204a-204n, 206a-206n, 208a-208n, and 210a-210n may also include other peripherals, such as keyboards, displays, microphones, and the like.

One feature of software 214a-214d is that it enables point-of-care physicians to submit pharmaceutical claims directly to the payor for direct reimbursement. The data required to implement this process includes the physician identification information, the patient identification information, the insurance identification number, and the product identification number. The physician identification information includes name, address, telephone number, FAX number, e-mail address, NPDS number, DEA number and NPI number. The patient identification information includes name, address, telephone number, age, gender and social security number. The insurance information includes carrier, policy number, and group number. The product information includes product name, NDC number, AWP number and SRP number. This information may be inserted into either Form 1500 or Form UDF in electronic format and capable of printing in hard copy.

In one aspect, the server 202*a* may be in communication with an adjudication computer system 240, and a translation system 242 that may host the NCPDP 5.1 data switch. Further, the server 202*a* may connect to a national switch, such as Mastercard computer system 244.

Figure 3:
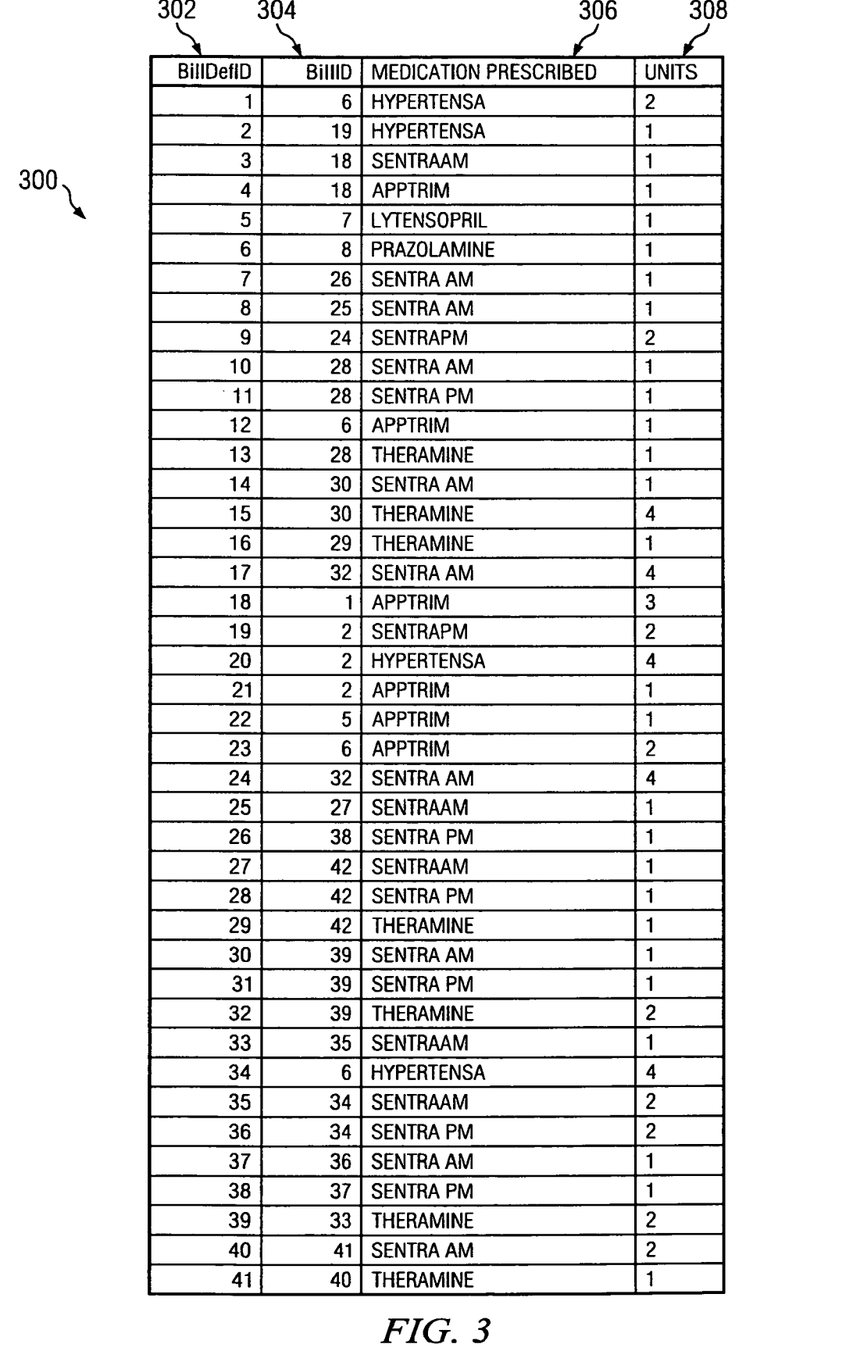
FIG. 3 illustrates an exemplary screen shot from a graphical user interface ("GUI") for submitting dispensed medication claims by point-of-care physicians according to an embodiment of the present invention.

FIG. 3 illustrates an embodiment 300 of an exemplary screen shot of a data report from a graphical user interface ("GUI") showing several columns and rows of data related to dispensed medications and related patient and dispensing point-of-care physician. Column 302 notes sequential line numbers for each row contained in column 302; each row pertaining to a separate dispensed medication related to a separate patient and dispensing point-of-care physician. Column 304 notes a value for each row that correlates to a particular patient and dispensing point-of-care physician. For example, the first row has a value of "6" in column 304 that correlates to a specific patient and their prescribing/dispensing point-of-care physician. In one aspect, the value contained in column 304 is a unique value that denotes a particular physician and a particular patient, thus it will usually be different from many of the other values contained in column 304.

Column 306 notes a particular dispensed medication for each row shown in the data report 300. For example, the first row of column 306 shows the medical food, "Hypertensa" as being dispensed by a particular physician to a particular patient associated with the value shown in the first row of column 304. Finally, column 308 notes the value of units dispensed by a particular physician to a particular patient. In another example, the third row of the data report 300 shows one unit of the medical food, "Sentraam" being dispensed by a physician to a patient correlating to the value, "18" as shown in column 304.

Turning to FIG. 4, an exemplary embodiment 400 of a screen shot of a Form UDF from a GUI showing several data fields relating to a particular patient and physician for submitting pharmaceutical claims by a point-of-care physician is shown. The Form UDF 400 may be in paper or electronic form for input of data by a user or point-of-care physician. Data field 402 notes the insurance payor that a particular pharmaceutical claim will be submitted by a particular point-of-care physician. Data filed 404 notes the particular logical switch where the pathway to a reimbursable bill is determined, such as NCPDP 5.1 compliant switch of Envoy Corporation. Data field 406 denotes a unique identification number associated with a particular patient that has been dispensed the dispensed medication. Data field 408 denotes a particular prescription reference number associated with the dispensed medication. Data field 410 denotes the date of service provided by the point-of-care physician to the patient. Data field 412 denotes the transaction type, such as prescription billing. Data field 414 denotes the transaction status, such as rejection. Other data values for this field may also include acceptance, suspension, and the like.

Data field 416 contains the data relating to the BIN number that are typically unique numbers issued by the American National Standards Institute that identifies the appropriate processor, the switch that forwards messages from the point-of-care physician to the processor and then returns the responses. Data field 418 includes information relating to the processor control number. Data field 420 contains information relating to the NPDS number for identifying the point-of-care physician's eligibility to enter a NCPDP 5.1 compliant switch. Data field 422 contains information relating to a software vendor ID. Data field 424 contains information relating to the transaction response status, such as "R" for rejected. Data fields 426, 428, and 430 may contain additional information relating to the transaction response, such as why the claim is rejected, accepted, etc. In this particular example, the claim is shown as being rejected for not being covered under Part D of Medicare. Also shown in this example is that the dispensed medication is a CMS excluded drug.

Data field 432 may include information relating to a EM&/Service reference qualifier. Data field 434 may contain information relating again to the prescription reference number. Data fields 436-446 may contain information relating to a specific patient's medical plan identification reference number, medical group plan identification number, cardholder last name, cardholder first name, and home plan information. In addition, data fields 448-480 may contain information relating to prescription/service reference qualifier, prescription/service number, product/service identification number, alternate identification data, prescription fill number, prescription days of supply, DAW/product selection code, date prescription written, number of refills authorized, level of service, prescription origin code, submission clarification code, unit dose indicator, quantity dispensed, prior authorization type code, and unit of measure. The values in each of these data fields are of the format and range commonly known to those skilled in the medical dispensing arts.

Data field 482 contains data relating to the ingredient cost submitted for reimbursement by a point-of-care physician. Data field 484 contains data relating to the basis of cost determination. Data field 486 contains data relating to the usual and customary charge associated with the dispensed medication. Data field 488 includes information relating to the prescriber identification qualifier. FIG. 5 illustrates an embodiment 500 of a continuation of the Form UDF 400 of FIG. 4. Data field 502 contains information relating to the database prescriber identification and data field 504 contains information relating to a 7E DUR/PPS code counter.

Referring to FIG. 6, an exemplary embodiment 600 of screen shot of a Form 1500 from a GUI showing several data fields relating to a particular patient and physician for submitting pharmaceutical claims by a point-of-care physician is shown. Data field 602 contains selections for several types of medical insurance payors, such as Medicare, Medicaid, CHAMPUS, CHAMPVA, Group Health Plan, FECA Black Lung, and Other. Similar to Form UDF described above, Form 1500 may be presented to a user or point-of-care physician in electronic form or paper form for completion. Data fields 604, 608, and 610 contain information relating to the particular insurance provider for a patient and data field 606 contains information relating to the patient's personal contact information. The medical insurance information may include: insured's identification number, insured's name, insured's address, group policy information, date of birth, insurance plan or program, and the like. In addition, Form 1500 contains data field 612 that contains information relating to a particular point-of-care physician's identification number, such as their NPI number.

Data field 614 preferably contains information relating to the location of the medical services and data field 616 contains the information relating to a diagnosis, such as a CPT diagnosis code. Data field 618 contains the information relating to the dates of service provided by the point-of-care physician to a particular patient associated with a particular Form 1500. Data field 620 includes information relating to the diagnosis code associated with the diagnosis arrived at by the point-of-care physician for a particular patient. Data field 622 includes information relating to the charges associated with the services or dispensed medication by the point-of-care physician. Data field 624 contains information relating to the number of days or units of dispensed medication for a particular patient. Data field 626 contains information relating to the total charges associated with the dispensed medication and data field 628 contains information relating to the amount paid to the point-of-care physician. Data field 630 contains information relating to a particular patient's account and data field 632 contains information relating to the point-of-care physician's signature and credentials.

Figure 7:
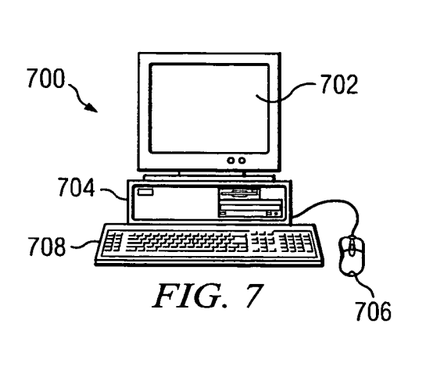
FIG. 7 illustrates an exemplary computer for displaying GUIs to a user for submitting dispensed medication claims by point-of-care physicians according to an embodiment of the present invention.

FIG. 7 illustrates an embodiment of a computer system 700 for use by a user or point-of-care physician to view and submit pharmaceutical claims for reimbursement. The computer system 700 typically includes a central processing unit 704 that contains memory, both volatile and non-volatile, and processor(s) for executing instructions stored on the processors and memories. The central processing unit 704 may also contain interfaces and modems for connecting with networks, such as the Internet. The central processing unit 704 is also connected to peripheral input devices such as a mouse 706, keyboard 708, and display 702. Other devices, such as handheld devices may be used in place of computer system 700 as are commonly known to those skilled in the computer arts.

Figure 8:
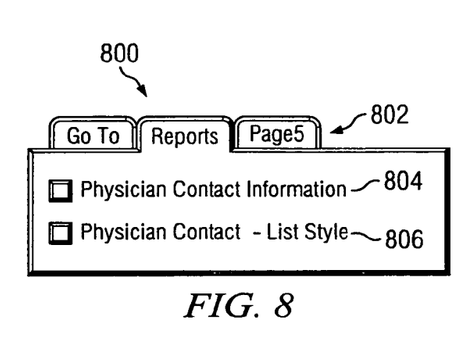
FIG. 8 illustrates an exemplary screen shot of a GUI including selections for physician contact information for submitting dispensed medication claims by point-of-care physicians according to an embodiment of the present invention.

Turning to FIG. 8, an exemplary embodiment 800 of a screen shot of a physician contacts display of a GUI is shown that may be displayed to a user or point-of-care physician. In this embodiment, physician contacts display 800 includes tabs 802 for navigating among different user interfaces or displays of the GUI, such as "Go To" and "Page 5." In addition, physician contacts display 800 may include a Physician Contact Information 804 link that when selected will display to a user or point-of-care physician related physician contact information. It may further display a Physician Contact—List Style 806 link that when selected displays additional selections relating to styles.

Figure 9:
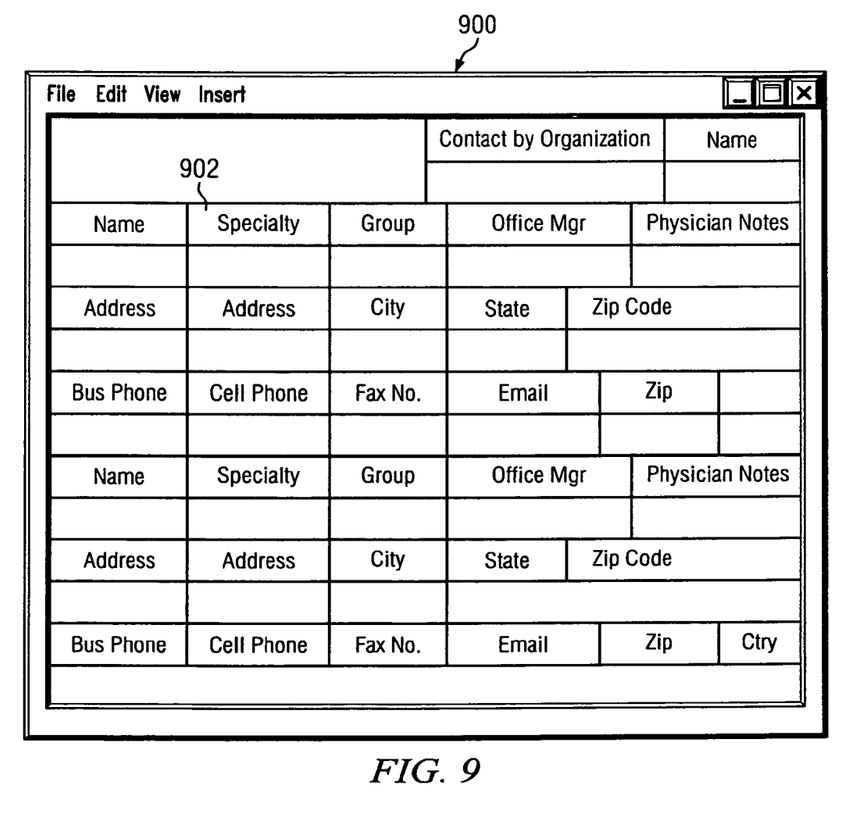
FIG. 9 illustrates an exemplary screen shot of a GUI including physician contact information for submitting dispensed medication claims by point-of-care physicians according to an embodiment of the present invention.

Referring to FIG. 9, an exemplary embodiment 900 of a screen shot of a physician contact information user interface is shown. Physician contact information user interface 900 may include information 902 relating to a particular physician among a collection of physicians. This information may include: name, specialty, group, office manager, physician notes, and address. In one aspect, one or more physicians may be displayed on one or more contact information user interfaces 900.

Figure 10:
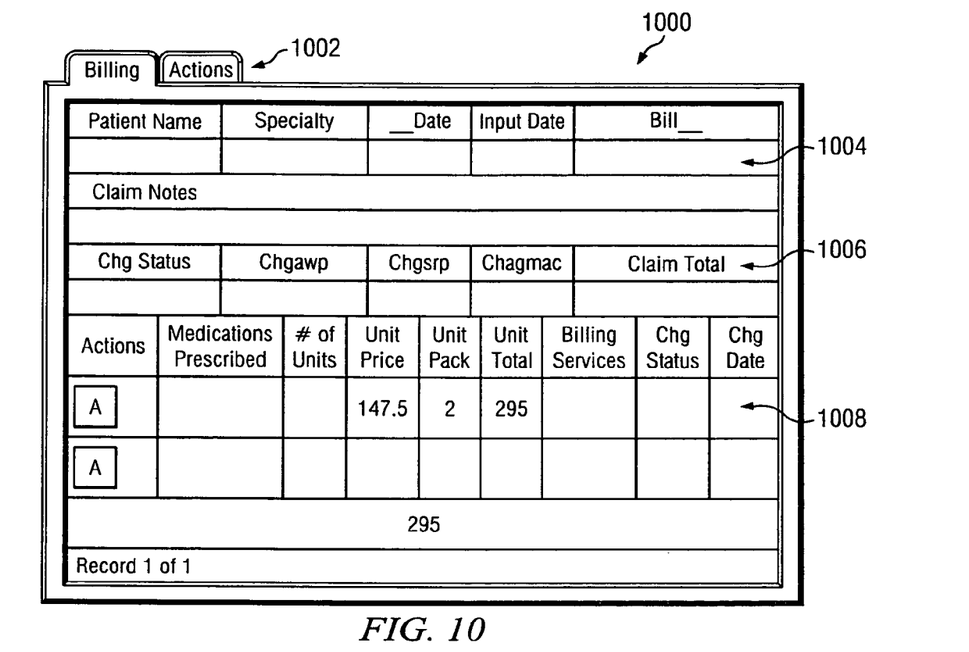
FIG. 10 illustrates an exemplary screen shot of a GUI including billing information for submitting dispensed medication claims by point-of-care physicians according to an embodiment of the present invention.

FIG. 10 illustrates an exemplary embodiment 1000 of a screen shot of a billing user interface having navigation tabs 1002 directed to billing user interface 1000 and possibly other screens or user interfaces as shown. Billing user interface 1000 may include point-of-care physician information 1004 and billing information 1006, such as charge status and charge total. Additional billing information 1008 may be displayed to a user or point-of-care physician relating to actions, medications prescribed, number of units, unit price, unit pack, unit total, billing services, charge status, and charge date.

Figure 11:
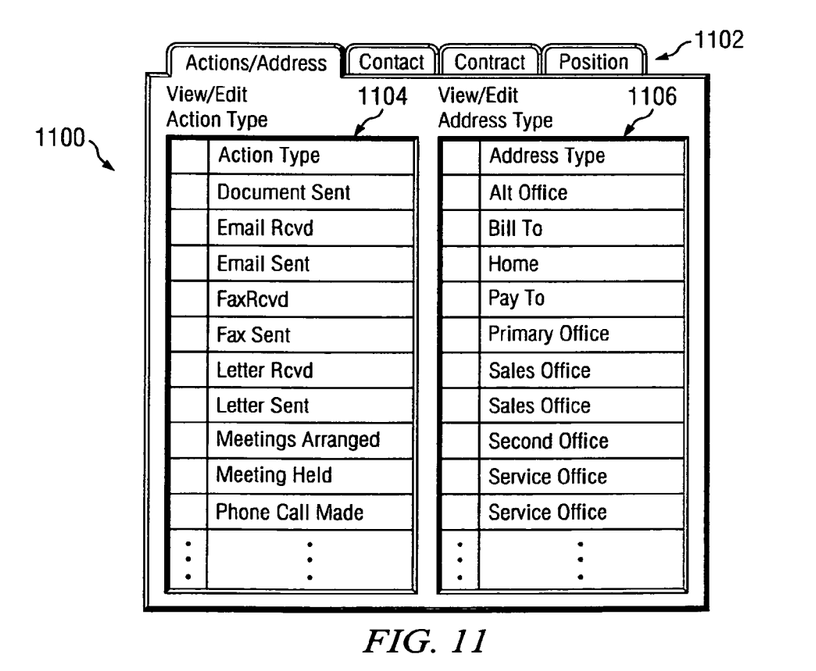
FIG. 11 illustrates an exemplary GUI screen shot of a GUI including editing information for submitting dispensed medication claims by point-of-care physicians according to an embodiment of the present invention.

FIG. 11 illustrates an exemplary embodiment 1100 of screen shot of an "Actions/Address" user interface. The Actions/Address user interface 1100 may include tabs 1102 for navigating to other user interfaces of the present physician dispensed medication claim submittal system. In one aspect, the Actions/Address user interface 1100 includes a section for viewing and/or editing action types, such as action type, document sent, email received, email sent, fax received, fax sent, letter received, letter sent, meetings arranged, meetings held, phone call made, and the like. In addition, Actions/Address user interface 1100 may include a section for viewing and/or editing address types, such as address type, alternate office, bill to, home, pay to, primary office, sales office, service office, and the like.

Figure 12:
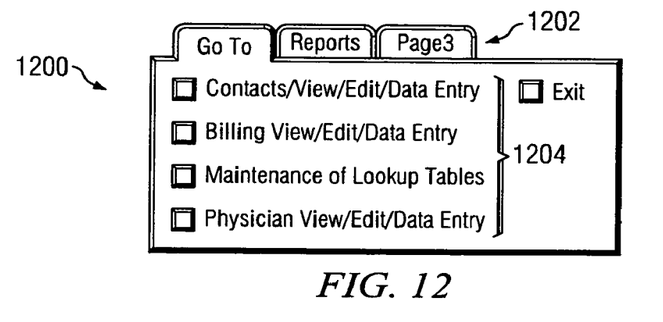
FIG. 12 illustrates an exemplary GUI screen shot of a GUI including general selections for submitting dispensed medication claims by point-of-care physicians according to an embodiment of the present invention.

FIG. 12 illustrates an exemplary embodiment 1200 of a screen shot of a "Go To" user interface. The Go To user interface 1200 may include tabs 1202 for navigating to other user interfaces of the present physician dispensed medication claim submittal system. In one aspect, the Go To user interface 1200 includes may include selections 1204, such as contacts/view/edit/data entry, billing view/edit/data entry, maintenance of lookup tables, physician view/edit/data entry, exit, and the like.

Figure 13:
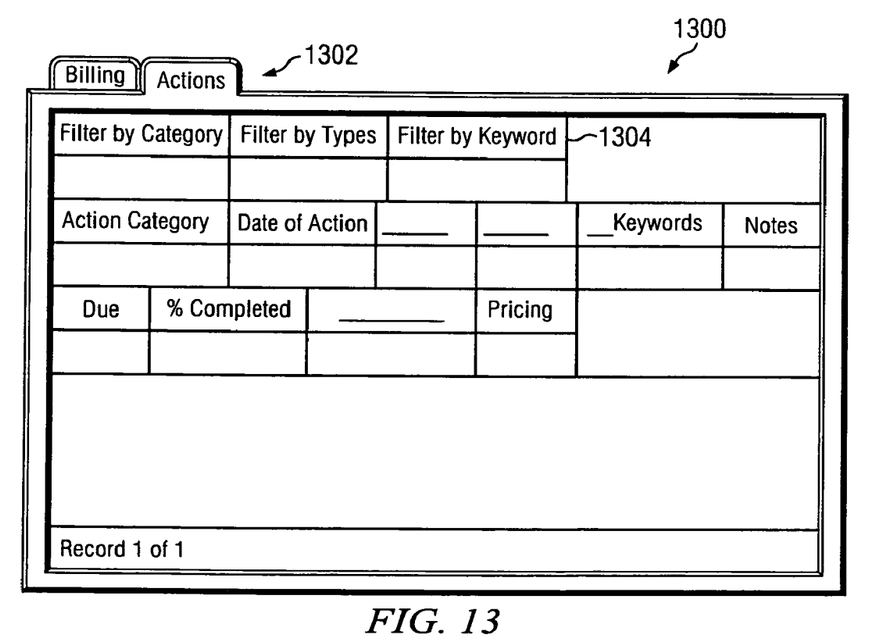
FIG. 13 illustrates an exemplary GUI screen shot of a GUI including actions information for submitting dispensed medication claims by point-of-care physicians according to an embodiment of the present invention.

FIG. 13 illustrates an exemplary embodiment 1300 of a screen shot of an "Actions" user interface. The Actions user interface 1300 may include tabs 1302 for navigating to other user interfaces of the present physician dispensed medication claim submittal system. In one aspect, the Actions user interface 1300 includes may include selections 1304 for searching and filtering data contained within the present physician dispensed medication claim submittal system.

Figure 14:
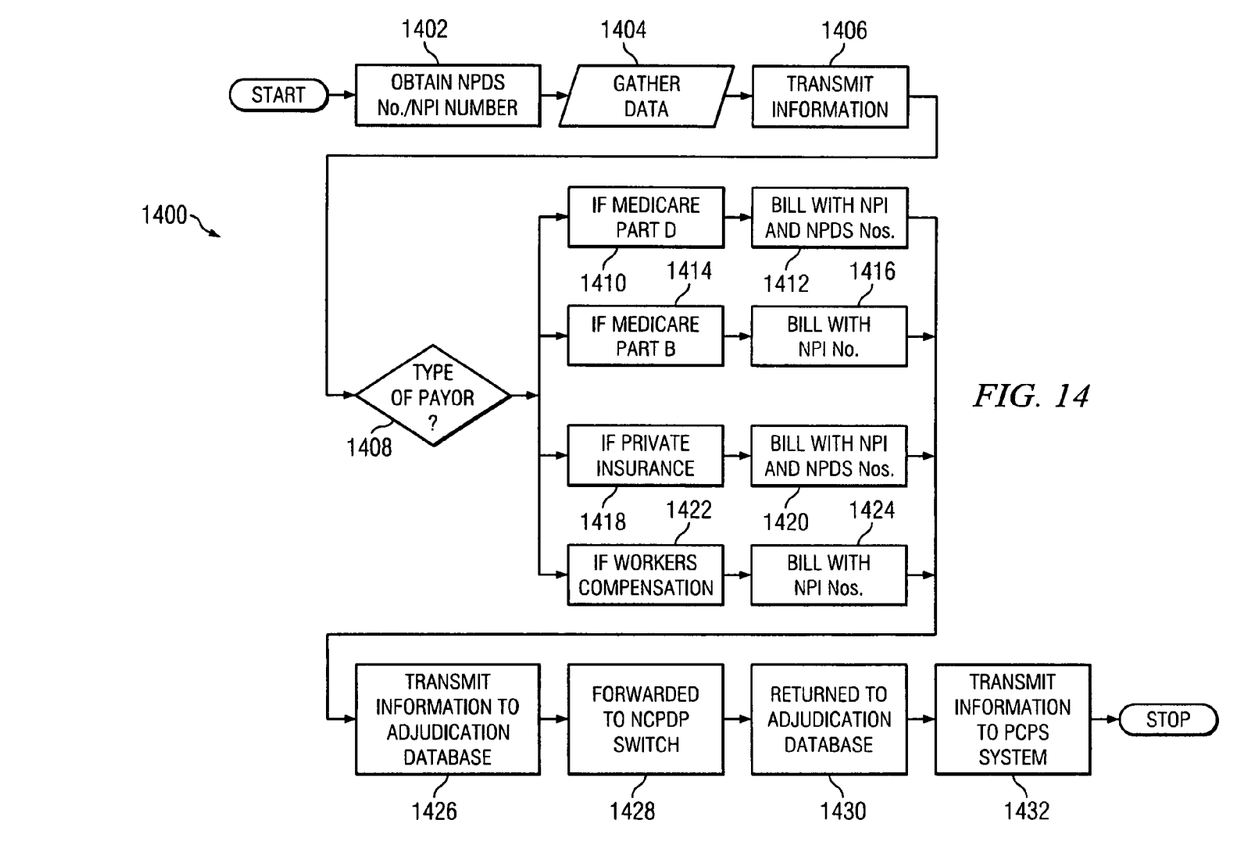
FIG. 14 illustrates a block diagram of an exemplary process for submitting dispensed medication claims by point-of-care physicians according to an embodiment of the present invention.

FIG. 14 illustrates a block diagram of an embodiment 1400 of an exemplary process for submitting pharmaceutical claims by a point-of-care physician according to an embodiment of the present invention. In step 1402, the physician dispensed medication claim submittal system displays a control panel or user interface to a point-of-care physician's computer display or in the form of a paper form. The data is either transmitted either through the computer network or by transmission of the form over a secure fax network The control panel may be displayed upon starting the user's computer 206a-206n, 208a-208n, and 210a-210n or by selecting an icon on their toolbar. Step 1402 includes displaying input fields/boxes and menus for entering data related to submitting pharmaceutical claims by a point-of-care physician. Some exemplary inputs displayed to the point-of-care physician include for example: field number, field name, field type, field format, and field length positions: (i) transaction format for prescription, which includes fields such as BIN, version number, transaction code, processor code, pharmacy number, group number, cardholder identification number, date of fill, and prescription number; (ii) response format for eligibility verification or prescription claim, which includes fields such as BIN, transaction code, response status, and response data; and (iii) claim reversal format, which includes fields, such as BIN, transaction code, processor code, pharmacy identification number, date of fill, and prescription number. Other NCPDP standard message formats include a worker's compensation claim format, a Medicaid claim format, a claim payable response format, and a claim captured response format. The present physician dispensed medication claim submittal system utilizes these NCPDP standard formats in implementing new functionality into the current system to enable claim input from physicians dispensing and selling pharmaceuticals. In addition, step 1402 the NPDS number is obtained from the service provider and the NPI number is obtained from the prescriber.

In one aspect, a point-of-care physician both prescribes and dispenses the dispensed medication, thus their role as a prescriber is identified by the NPI number while their role of dispenser or provider is identified by the NPDS number. A submitted claims will then have both the NPI and NPDS number. The present physician dispensed medication claim submittal system is different than present day practices where a pharmacist uses a physician identification number on the written prescription along with the pharmacists NCPDP. Once an NPDS number is obtained, the physician is recognized as if the physician is a pharmacy. The present physician dispensed medication claim submittal system then uses the NPDS number to interact with the switches designed for pharmacies as described below. The NPDS number is obtained from the National Council for Prescription Drug Programs ("NCPDP") of Phoenix, Ariz. A form specific to physicians is obtained, prepared and fee submitted.

A physician obtains these two types of identification numbers that uniquely define the physician compared to other physicians as both a prescriber and a provider. Such prescriber numbers include the NPI number, DEA number, State license number, and Medicare UPIN number. The physician then obtains a unique provider number called the NPDS number that identifies the physician as a medication provider. The NPDS number allows the electronic switch to identify the physician as a medication provider. The form of the number is identical in format to the number that uniquely identifies pharmacies.

In step 1404, a user, such as a data processing technician, uses the data from a point-of-care physician and inputs the data into the physician dispensed medication claim submittal system, including physician data, patient data, and prescription data. Typically, a physician gathers this data by examining a patient and selecting the appropriate treatment for the patient. The appropriate treatment may also include the dispensed medications to be dispensed to the patient and any information related to the dispensed medications. It further may include gathering insurance coverage information from the patient as well. Some of this information may include the National drug code identifier code ("NDC") number, the corresponding listed average wholesale price "AWP") and suggested retail price ("SRP") of the medication and the unit quantities of the dispensed medications prescribed.

As described herein, two forms, the Form UDF and the Form 1500, exist currently to facilitate the transmission of data to the logical switch. Generally, the Form 1500 was originally designed for Medicare billing to identify a particular physician and their related services. Over time, it has become a popular billing form to identify physician services, including pharmaceuticals billed as part of the physician services. The Form UDF is designed specifically for pharmaceutical billing and prior to this invention was not used by physicians who did not possess a NPDS number. In addition to those forms and user interfaces disclosed herein, other forms and user interfaces are contemplated and incorporated herein for enabling such transmission of data.

In step 1406, the data gathered in steps 1402 and 1404 are transmitted in the form of a claim to the switch of the present physician dispensed medication claim submittal system. The compliant interface of the present physician dispensed medication claim submittal system allows the submitted claim to enter through a decision gate to an existing Automated Clearing House ("ACH") system currently utilized by banks to credit their merchants for credit card sales combined with the well-established securitized asset financial market. In step 1408, an inquiry is made regarding the form of the claim that is submitted to the payor. Some of the forms include as disclosed above, a physician service form called a Form 1500 (FIG. 6) and a universal computerized drug form (UDF). In addition to these forms, the logic switch must determine the type of insurance with medication benefit that the patient has including PPO private insurance, HMO private insurance, Medicare Part B, Medicare Part D, Champus, and Medicaid. The switch evaluates the patients insurance information and determines the pathway particularly since each insurance form uses a different form and there is no universal form.

Once the pathway is determined, the form is defined. Each form has different fields and requirements for placement of data into the forms. A particular aspect of the current invention is the determination of the data criteria for the billing forms. For example, the NPDS number goes in a particular field in the Form 1500 and in another field in the Form UDF. In step 1410, the present physician dispensed medication claim submittal system determines if the pharmaceutical claim is to be submitted under Medicare Part D. If so, then in step 1412, the present physician dispensed medication claim submittal system submits the claim with the NPI and NPDS numbers. In step 1414, the present physician dispensed medication claim submittal system determines if the pharmaceutical claim is to be submitted under Medicare Part B. If so, then in step 1416, the present physician dispensed medication claim submittal system submits the claim with the NPI number. In step 1418, the present physician dispensed medication claim submittal system determines if the pharmaceutical claim is to be submitted under private insurance. If so, then in step 1420, the present physician dispensed medication claim submittal system submits the claim with the NPI and NPDS numbers. In step 1422, the present physician dispensed medication claim submittal system determines if the pharmaceutical claim is to be submitted under workers compensation. If so, then in step 1424, the present physician dispensed medication claim submittal system submits the claim with the NPI number. In each of these steps above, a user may enter data into the physician dispensed medication claim submittal system in response to displays from the physician dispensed medication claim submittal system regarding these different reimbursement options.

In step 1426, the present physician dispensed medication claim submittal system submits the claim to the adjudication database. Typically, the adjudication computer system 240 may be a database of payors that is maintained and include the private insurance payors and Medicare payors. The database for each payor may include each of the plans and enrollment for their members. In this step, the contract between the point-of-care physician and the payor is verified. Typically, many of the insurance payors require contracts between the point-of-care physician and the payor, thus it may need to be verified. The present physician dispensed medication claim submittal system obtains and manages the contracts between the point-of-care physicians and the payors. The switch currently provides the means to transfer electronic claim messages and their adjudicated responses between thousands of service providers and dozens of processors. In one embodiment, the present physician dispensed medication claim submittal system uses a switch that captures all on-line transactions as they are originated by point-of-care physicians, copies all transactions that relate to a client provider, time stamps the claims, and forwards them to the appropriate processor designated by the BIN. In addition, the present physician dispensed medication claim submittal system also captures and copies all on-line adjudicated transactions as they are approved by the processors and routed back to the originating point-of-care physician pharmacy by the switch. These claims and replies are retained for further processing. The captured claims and responses are "cleaned" of duplicates and other system-related anomalies such as time-outs, and reversals are processed. In another embodiment, all or some of these switch functions are performed by a third party, such as NDC. Typically, the verification process in performed by the systems and databases maintained at these levels. In step 1428, the claim is forwarded to the NCPDP switch as disclosed herein.

In step 1430, the present physician dispensed medication claim submittal system returns the claims from the adjudication database. It also provides a special purpose switch that provides a cost efficient mechanism for handling the flow of industry standard format messages. The special purpose switch interfaces with the many third-party software applications that may also provide the on-line adjudication functionality. Additionally, the present physician dispensed medication claim submittal system provides the means for point-of-contact physicians to request information from PCPS regarding their transaction and payment activity and payor, obligor, and plan coverage for responding and supplying the information quickly to point-of-care physician, without the need to modifying the existing NCPDP standard protocols. These means provide point-of-care physicians new and important capability of obtaining immediate, up-to-date information regarding their claim transactions. In one embodiment, the present physician dispensed medication claim submittal system interoperates with existing software used in physician offices, for example the electronic message control protocols established by the NCPDP.

In step 1432, responsive to the physician claim submitted by the physician claims processor, an NCPDP-formatted adjudication message is then transmitted by the processor receiving the claim back through the same channels. This then is transmitted by the claims processor to the originating physician. An adjudication summary may be created as well for the point-of-care physician. The adjudication is an evaluation of the validity of a claim by reference to the patient eligibility and formulary rules of a plan, such as drug products allowed, types of permitted drug interactions and dosages, and drug prices, which will be reimbursed by a particular plan. The adjudication message normally contains adjudication/authorization information, the unique prescription number and the previously agreed upon price for that prescription. An adjudication message transmitted by a processor indicates the following three items of information about the claim: (i) that it has been received by the processor; (ii) that it has been reviewed by the processor; and (iii) that it has been indicated for disposition in one of three ways, namely approval, rejection, or suspension.

In step 1432, the present physician dispensed medication claim submittal system keeps track of the claims and payments adjudicated by the adjudication database, payor reports obtained, further correspondence with the payor, further review of claims and the subsequent payments sent to the point-of-care physicians. It further administers and pursues non-payment of claims that have been adjudicated. It also reconciles the claims and payments sent to point-of-care physicians. In addition, the present physician dispensed medication claim submittal system has a message switching and customer service functionality. Further data is processed in this module including patient internal ID, patient name, physician name, physician ID numbers, bill method, bill total, bill ID, bill date, dispense date product IDs, amount of each claim, claim status and notes concerning contacts with Payors.

The following non-limiting examples of the present physician dispensed medication claim submittal system are provided below.

EXAMPLE 1

Medicare Part D Claim

An internal medicine physician dispensed a bottle of generic lisinopril to a 66-year old female. The physician gathered the patient information including insurance information. The physician transmitted to the present physician dispensed medication claim submittal system the three sets of information including physician identifiers, patient information, and drug codes. The drug codes included: NDC numbers, AWP pricing and units dispensed. The patient information included both Medicare Part B and Part D coverage. The physician identifiers included the NPDS number and the NPI number. The information was entered into the payor database through the physician dispensed medication claim submittal system interface. The switch of the physician dispensed medication claim submittal system defined the insurance as Part D Medicare. The NCPDP 5.1 software was selected for transmission to the switches. The data was successfully transmitted to the payor database and an adjudication was obtained. The claim was initially declined because the physician did not have a contract with the payor. The payor was contacted, a contract was obtained agreed to by the two parties. The claim was then submitted via the physician dispensed medication claim submittal system interface to the payor database and claim approval obtained. The data was then transmitted to the payor via the NCPDP 5.1 data link. The approval was obtained and payment was received within three weeks.

EXAMPLE 2

Medicare Part B Claim

An internal medicine physician dispensed a bottle each of a medical Food to a 68-year old female. The physician gathered the patient information including insurance information. The physician transmitted to the physician dispensed medication claim submittal system the three sets of information including physician identifiers, patient information and the drug codes. The drug codes included NDC numbers, AWP pricing, and units dispensed. The patient information included both Medicare Part B and Part D coverage. The physician identifiers included the NPDS number and the NPI number. The switch of the physician dispensed medication claim submittal system defined the insurance as Part B Medicare. The information was a Form 1500 through the physician dispensed medication claim submittal system interface. The NCPDP 5.1 software was selected for transmission to the switches. The data was successfully transmitted to the payor database and an adjudication obtained. The claim was accepted for payment under Part B Medicare.

EXAMPLE 3

PPO Insurance Claim

An internal medicine physician dispensed a bottle each of a medical Food to a 46-year old female. The physician gathered the patient information including insurance information. The physician transmitted to the physician dispensed medication claim submittal system the three sets of information including physician identifiers, patient information, and the drug codes. The drug codes included NDC numbers, AWP pricing, and units dispensed. The patient information included private insurance coverage. The physician identifiers included the NPDS number and the NPI number. The switch of the physician dispensed medication claim submittal system defined the insurance as PPO private insurance. The information was entered a Form 1500, including an NPI number, through the physician dispensed medication claim submittal system interface. The NCPDP 5.1 software was selected for transmission to the switches. The data was successfully transmitted to the payor database and an adjudication obtained. The claim was accepted for payment under PPO insurance.

EXAMPLE 4

PPO Insurance Claim

An orthopedic surgeon dispensed a bottle each of a medical Food to a 68-year old male with a work related injury. The physician gathered the patient information including insurance information. The physician transmitted to the physician dispensed medication claim submittal system the three sets of information including physician identifiers, patient information, and the drug codes. The drug codes included NDC numbers, AWP pricing, and units dispensed. The patient information included both California Workers Compensation coverage. The physician identifiers included the physician DEA number. The switch of the physician dispensed medication claim submittal system defined the insurance as Workers Compensation. The information was a Form 1500 through the physician dispensed medication claim submittal system interface. The paper claim method was selected for transmission to the switches. The data was successfully transmitted to the payor. The claim was accepted for payment under California Workers Compensation Insurance.

EXAMPLE 5

Private Insurance

An general practitioner physician dispensed a Co-packed Medical Food with a generic pharmaceutical to a 36-year old female. The physician gathered the patient information including insurance information. The physician transmitted to the physician dispensed medication claim submittal system the three sets of information including physician identifiers, patient information, and drug codes. The drug codes included NDC numbers, AWP pricing, and units dispensed. The patient information included private insurance coverage. The physician identifiers included the NPDS number and the NPI number. The information was entered into the payor database through the physician dispensed medication claim submittal system interface. The switch of the physician dispensed medication claim submittal system defined the insurance as private insurance using the NPDS identifier for the provider and NPI for the prescriber. The NCPDP 5.1 software was selected for transmission to the switches. The data was successfully transmitted to the payor database and an adjudication obtained. The claim was then submitted via the interface of the physician dispensed medication claim submittal system to the payor database and claim approval obtained. The data was then transmitted to the payor via the NCPDP 5.1 data link The approval was obtained.

Although there has been described what is at present considered to be the preferred embodiments of the physician dispensed medication claim submittal system and methods for submitting pharmaceutical claims by point-of-care physicians, it will be understood that the physician dispensed medication claim submittal system can be embodied in other specific forms without departing from the spirit or essential characteristics thereof. For example, other networks and computer systems can be used, other than those described herein could be used without departing from the spirit or essential characteristics of the present system and method for submitting pharmaceutical claims by point-of-care physician. The present embodiments are, therefore, to be considered in all aspects as illustrative and not restrictive. The scope of the invention is indicated by the appended claims rather than the foregoing description.

What is claimed:

1. A computer system for submitting a claim for a dispensed medication to a patient by a point-of-care physician comprising:
    one or more non-transitory computer-readable media having tangibly embodied thereon one or more computer-executable instructions that are structure such that, when executed by one or more processors of said computer system, the computer system is configured to perform the following:
    an act of acquiring at least one of the group consisting of a national provider identifier number and a non-pharmacy dispensing site number for said point-of-care physician;
    an act of displaying to a user a selection of data fields relating to said claim;
    an act of inputting into said data fields data relating to said claim including a payor, said dispensed medication, and said at least one of the group consisting of said national provider identifier number, said non-pharmacy dispensing site number;
    responsive to said inputted payor, an act of producing an electronic form of one of a 1500 form and a universal drug form based on said payor, said producing said electronic form comprising inputting said at least one of said national provider identifier number and said non-pharmacy dispensing site number in a predetermined field in said produced electronic form of one of said 1500 form and said universal drug form;
    an act of transmitting to a logic switch said produced electronic form containing said claim containing said payor, said dispensed medication, and said at least one of the group consisting of said national provider identifier number, said non-pharmacy dispensing site number identifying said point-of-care physician for determining the processor for said claim;
    an act of determining the pathway for said claim, said act of determining comprising:
        responsive to said payor being Medicare Part D, processing said national provider identifier number and said non-pharmacy dispensing site number;
        responsive to said payor being Medicare Part B, processing said national provider identifier number;
        responsive to said payor being private insurance, processing said national provider identifier number and said non-pharmacy dispensing number;
        responsive to said payor being worker's compensation, processing said national provider identifier number;
    an act of processing by said payor said claim containing said at least one of the group consisting of a national provider identifier number and a non-pharmacy dispensing site number to identify said point-of-care physician; and
    responsive to said act of processing, an act of transmitting to said point-of-care physician an adjudication regarding said claim.

2. The computer system for submitting a claim for a dispensed medication to a patient by a point-of-care physician of claim 1 wherein said act of transmitting further comprises
    transmitting to said payor with a computerized NCPDP 5.1 link.

3. The computer system for submitting a claim for a dispensed medication to a patient by a point-of-care physician of claim 1 wherein said payor is selected from the group consisting of PPO private insurance, HMO private insurance, Champus, and Medicaid.

4. The computer system for submitting a claim for a dispensed medication to a patient by a point-of-care physician of claim 1 wherein said data fields are selected from the group consisting of transaction format for prescription, BIN, version number, transaction code, processor code, pharmacy number, group number, cardholder identification number, date of fill, prescription number, response format, response status, response data, claim reversal format, date of fill, prescription number, worker's compensation claim format, Medicare claim format, claim payable response format, and claim captured response format.

5. The computer system for submitting a claim for a dispensed medication to a patient by a point-of-care physician of claim 1 further comprising:
an act of reimbursing said point-of-care physician for said submitted pharmaceutical or Medical Food claim.

6. The computer system for submitting a claim for a dispensed medication to a patient by a point-of-care physician of claim 1 further comprising:
an act of verifying the existence of a contract between said point-of-care physician and said payor.

7. The computer system for submitting a claim for a dispensed medication to a patient by a point-of-care physician of claim 1 further comprising:
an act of obtaining a contract between said point-of-care physician and said payor.

8. The computer system for submitting a claim for a dispensed medication to a patient by a point-of-care physician of claim 1 wherein said adjudication comprises a message containing information related to said processed claim selected from the group consisting of status of receipt by said one or more processors, status of review by said processor, and status of disposition.

9. An electronic computer system for submitting a claim for a dispensed medication to a patient by a point-of-care physician comprising:
an electronic input device for producing input signals;
a display;
an electronic memory storing at least one of the group consisting of national provider identifier number, non-pharmacy dispensing site number, transaction format for prescription, BIN, version number, transaction code, processor code, pharmacy number, group number, cardholder identification number, date of fill, prescription number, response format, response status, response data, claim reversal format, date of fill, prescription number, worker's compensation claim format, Medicare claim format, claim payable response format, and claim captured response format; and
an electronic processor communicating with said memory and said display and responsive to the input signals to:
direct said display to display a data field relating to said at least one of said group consisting of national provider identifier number, non-pharmacy dispensing site number, transaction format for prescription, BIN, version number, transaction code, processor code, pharmacy number, group number, cardholder identification number, date of fill, prescription number, response format, response status, response data, claim reversal format, date of fill, prescription number, worker's compensation claim format, Medicare claim format, claim payable response format, and claim captured response format;
receive input into said data field relating to said claim including a payor, said dispensed medication, and said at least one of the group consisting of said national provider identifier number, said non-pharmacy dispensing site number;
responsive to said inputted payor, produce an electronic form of one of a 1500 form and a universal drug form based said payor, said producing said electronic form comprising inputting said at least one of said national provider identifier number and said non-pharmacy dispensing site number in a predetermined field in said produced electronic form of one of said 1500 form and said universal drug form;
transmit to a logic switch said produced electronic form containing said claim containing said at least one of the group consisting of a national provider identifier number, a non-pharmacy dispensing site number identifying said point-of-care physician for determining the processor for said claim;
determine the pathway for said claim, said determine comprising:
responsive to said payor being Medicare Part D, process said national provider identifier number and said non-pharmacy dispensing site number;
responsive to said payor being Medicare Part B, process said national provider identifier number;
responsive to said payor being private insurance, process said national provider identifier number and said non-pharmacy dispensing number;
responsive to said payor being worker's compensation, process said national provider identifier number;
process by said payor said claim containing said at least one of the group consisting of a national provider identifier number and a non-pharmacy dispensing site number to identify said point-of-care physician; and
responsive to said processing, transmit to said point-of-care physician an adjudication regarding said claim.

10. The electronic computer system for submitting a claim for a dispensed medication to a patient by a point-of-care physician of claim 9 wherein
said transmit further comprises a computerized NCPDP 5.1 link.

11. The electronic computer system for submitting a claim for a dispensed medication to a patient by a point-of-care physician of claim 9 wherein said payor is selected from the group consisting of PPO private insurance, HMO private insurance, Champus, and Medicaid.

12. The electronic computer system for submitting a claim for a dispensed medication to a patient by a point-of-care physician of claim 9 wherein the electronic processor is further responsive to input signals to:
verify the existence of a contract between said point-of-care physician and said payor.

13. The electronic computer system for submitting a claim for a dispensed medication to a patient by a point-of-care physician of claim 9 wherein the electronic processor is further responsive to input signals to:
obtain a contract between said point-of-care physician and said payor.

14. The electronic computer system for submitting a claim for a dispensed medication to a patient by a point-of-care physician of claim 9 wherein said adjudication comprises a message containing information related to said processed claim selected from the group consisting of status of receipt by said processor, status of review by said processor, and status of disposition.

* * * * *